(12) United States Patent
Bernhardt et al.

(10) Patent No.: US 8,618,316 B1
(45) Date of Patent: Dec. 31, 2013

(54) LOW TEMPERATURE RAMP RATE ESTER QUAT FORMATION PROCESS

(75) Inventors: Randal J Bernhardt, Antioch, IL (US); Michael R Terry, Gurnee, IL (US)

(73) Assignee: Stepan Company, Northfield, IL (US)

( * ) Notice: Subject to any disclaimer, the term of this patent is extended or adjusted under 35 U.S.C. 154(b) by 1670 days.

(21) Appl. No.: 11/073,022

(22) Filed: Mar. 3, 2005

Related U.S. Application Data

(60) Provisional application No. 60/550,376, filed on Mar. 5, 2004.

(51) Int. Cl.
 C07C 235/86 (2006.01)
 C07C 237/50 (2006.01)
 C11D 3/26 (2006.01)

(52) U.S. Cl.
 USPC .............. 554/52; 510/339; 510/123; 510/126

(58) Field of Classification Search
 None
 See application file for complete search history.

(56) References Cited

U.S. PATENT DOCUMENTS

| | | | |
|---|---|---|---|
| 3,915,867 A | 10/1975 | Kang | |
| 4,830,771 A | 5/1989 | Ruback | |
| 5,023,003 A | 6/1991 | Yamamura | |
| 5,512,572 A | 4/1996 | Haikala | |
| 5,545,340 A | 8/1996 | Wahl | |
| 5,562,849 A | 10/1996 | Wahl | |
| 5,574,179 A | 11/1996 | Wahl | |
| 5,609,167 A | 3/1997 | Hansen | |
| 5,750,492 A | 5/1998 | Contet | |
| 5,830,845 A | 11/1998 | Trinh | |
| 5,869,716 A | 2/1999 | Pi Subirana | |
| 5,916,863 A * | 6/1999 | Iacobucci et al. | 510/329 |
| 6,037,315 A * | 3/2000 | Franklin et al. | 510/123 |
| 6,770,608 B2 | 8/2004 | Franklin | |

FOREIGN PATENT DOCUMENTS

| | | |
|---|---|---|
| DE | 4413431 | 10/1995 |
| EP | 0295385 | 12/1988 |
| EP | 0370675 | 5/1990 |
| EP | 0550361 | 7/1993 |
| EP | 0675941 | 7/1994 |
| EP | 0900260 | 10/2001 |
| FR | 2054337 | 4/1971 |
| WO | WO 91/01295 | 2/1991 |
| WO | WO 91/12364 | 8/1991 |
| WO | WO 93/10748 | 6/1993 |
| WO | WO 93/21291 | 10/1993 |
| WO | WO 94/14935 | 7/1994 |
| WO | WO 94/20597 | 9/1994 |
| WO | WO 95/25713 | 9/1995 |
| WO | WO 97/34975 | 9/1997 |

OTHER PUBLICATIONS

Kao Notice of Opposition, Oct. 31, 2001.
Procter & Gamble Notice of Opposition, Jul. 25, 2002.
Stepan Europe "D4" Intra Company Correspondence, submitted Jul. 31, 2002.
Stepan Europe "D5" Intra Company Correspondence, submitted Jul. 31, 2002.
Akzo Nobel letter, Jun. 6, 2003.
Akzo Nobel letter, Jun. 26, 2003.
Annex to the Summons to Attend Oral Proceedings, Aug. 7, 2003.
Maiwald Letter on behalf of Stepan Europe, Aug. 5, 2004.
Maiwald Letter on behalf of Stepan Europe, Aug. 16, 2004.
Maiwald Letter on behalf of Stepan Europe, Aug. 18, 2004.
Akzo Statement of Grounds of Appeal, Feb. 18, 2005.
Submission filed on behalf of Cognis, Jul. 14, 2005.
Submission filed on behalf of Cognis, Jul. 14, 2005 (English).
Hoffman-Eitle (Kao) Observations on the Statement Setting Out the Grounds of Appeal, Jul. 26, 2005.
Maiwald (Stepan) Response to the Statement of Grounds of Appeal, Jul. 26, 2005.
Kirk-Othmer Encyclopedia of Chemical Technology, 4th Edition, vol. 10, p. 267 (John Wiley & Sons 1993).

* cited by examiner

*Primary Examiner* — Yate K Cutliff

(74) *Attorney, Agent, or Firm* — McAndrews, Held & Malloy, Ltd.

(57) ABSTRACT

Esterquats (reaction products of a fatty acid source and a trialkanolamine) having a desirable distribution of mono-, di-, and tri-quat esters, such as at least 55 wt. % of the diester and at most 25% of the triester, can be produced by heating a trialkanolamine and a fatty acid source at a temperature ramp rate of 0.4° C. per minute or less. This result can be achieved, for example, by reducing the amount of catalyst to a suboptimal amount for rapid formation of the quat diester.

20 Claims, No Drawings

LOW TEMPERATURE RAMP RATE ESTER QUAT FORMATION PROCESS

PRIORITY CLAIM

This application claims priority to a provisional patent application, U.S. Ser. No. 60/550,376, filed Mar. 5, 2004. The entire provisional patent application is incorporated here by reference to provide continuity of disclosure.

BACKGROUND

United States Patent Application 20020025915 A1, Franklin et al., par. 0025, states, in part: "Triester formation in the esteramine mixture can be minimized by accelerating the heat up rate in the esterification reaction of fatty acids with alkanolamines. Typically, the accelerated heat up rate of greater than about 0.4° C. per minute, more preferably greater than about 0.8° C. per minute, and still more preferably greater than about 1.25° C. per minute from a temperature of about 70° C. to a temperature in a range of from between 170° C. to 250° C. is effective in minimizing triester formation in the esteramine mixture." Franklin et al. further states in part at par. 0035: "The quaternary ammonium compounds according to the present invention can generally be prepared by reacting at least one $C_{12}$-$C_{22}$ fatty acid having a IV of from 20-90 with an alkanol amine in the presence of an acid catalyst. * * * A heat up rate of at least about 0.8° C. per minute is employed in order to minimize triester formation. The esterification products are subsequently alkylated in order to obtain the quaternary ammonium product." The Franklin et al., published patent application is hereby incorporated herein by reference in its entirety for its disclosure of quat esters of tri(lower alkanol) amines such as triethanolamine and fatty acid sources, formulations containing such quat esters and optionally other ingredients, and methods for making such quat esters of triethanolamine and fatty acid sources.

EP 0 675 941, also published as WO94/14935, and WO 91/01295, are also pertinent here, and are incorporated here by reference in their entireties for their disclosure of quat esters of tri(lower alkanol) amines such as triethanolamine and fatty acid sources, formulations containing such quat esters and optionally other ingredients, and methods for making such quat esters of triethanolamine and fatty acid sources.

Esterquat products have been made outside the United States for many years by various producers, including Stepan Company, using ramp up rates below the rates required by the Franklin et al. published application.

SUMMARY OF THE INVENTION

The present inventors have discovered that esterquats having a desirable distribution of mono-, di-, and tri-quat esters, such as at least 55 wt. % of the diester and at most 25% of the triester, can be produced at lower ramp rates than the "greater than about 0.4° C. per minute" minimum ramp rate specified in the Franklin et al. patent, as by reducing the amount of catalyst used to a suboptimal amount for rapid formation of the quat diester. The inventors have discovered that the rate of formation of the triester is reduced more than the rate of formation of the diester as the result of reducing the amount of catalyst below the optimal level for rapid formation of the quat diester.

DETAILED DESCRIPTION

Esterquats are made by combining a fatty acid source and an alkanolamine, typically at a starting temperature at which the fatty acid source is molten, optionally adding a catalyst, then heating the reaction mixture while drawing vacuum until the desired endpoint(s), such as acid value and final alkalinity value, are reached. The resulting esteramine intermediate is then quaternized using an alkylating agent, yielding an esterquat product. The esterquat product is a mixture of quaternized monoester, diester, and triester components and optionally some amount of one or more reactants, intermediates, and byproducts.

The weight percentages of the monoester, diester, and triester quats in the product are reported on the basis of the total weight of the three. Thus, the sum of these three percentages is 100%.

The presently contemplated products have a minimum weight percentage of diester quat of at least 55%, optionally at least 60%, optionally at least 65%, optionally at least 70% optionally at least 75%, optionally at least 80%, optionally at least 85%, optionally at least 90%, optionally at least 95% by weight. (All percentages stated in this specification are by weight unless otherwise indicated.) The presently contemplated products have a maximum weight percentage of diester quat of at most 55%, optionally at most 60%, optionally at most 65%, optionally at most 70% optionally at most 75%, optionally at most 80%, optionally at most 85%, optionally at most 90%, optionally at most 95%, optionally at most 100% by weight.

The presently contemplated products have a maximum weight percentage of triester quat of at most 25%, optionally at most 20%, optionally at most 18%, optionally at most 16%, optionally at most 15%, optionally at most 14%, optionally at most 12%, optionally at most 10%, optionally at most 8%, optionally at most 6%, optionally at most 5%, optionally at most 4%, optionally at most 2% by weight. The presently contemplated products have a minimum weight percentage of triester quat of 0%, optionally 5%, optionally 10%, optionally 15%, optionally 20% by weight.

The presently contemplated products have as a weight percentage of monoester quat the balance required to yield 100% quat esters.

The present inventors specifically contemplate any combination of any lower limit set out in this specification and any equal or greater upper limit set out in this specification as an operative range of the present invention. The inventors further specifically contemplate any combination of two ranges set out in this specification that is mathematically possible. For example, if the range of diester quat is 55% to 75% by weight, the corresponding range of the triester quat can be as low as 0% and as high as 45% by weight, or any lesser included range such as 0% to 24% by weight. In this example the corresponding range of the monoester quat would also be as low as 0% and as high as 45% by weight, or any included range such as 0% to 28% by weight.

The "ramp rate" is defined here as the average rate of temperature increase of the reaction mixture comprising a fatty acid source and a trialkanolamine over a period of at least four hours, from the initial temperature used to liquefy the fatty acid source to the highest (and final, in one alternative embodiment) reaction temperature employed in the process. An exemplary starting temperature is in the range of about 60 to about 70° C. The highest reaction temperature may be any value within a range of roughly 70° C. to 250° C.

Specifically, a ramp rate upper limit of 0.4° C. per minute or less, alternatively about 0.4° C. per minute, alternatively less than 0.4° C. per minute, alternatively 0.35° C. per minute, alternatively about 0.35° C. per minute, alternatively less than 0.35° C. per minute, alternatively 0.3° C. per minute, alternatively about 0.3° C. per minute, alternatively less than 0.3°

C. per minute, alternatively 0.25° C. per minute, alternatively about 0.25° C. per minute, alternatively less than 0.25° C. per minute, alternatively 0.2° C. per minute, alternatively about 0.2° C. per minute, alternatively less than 0.2° C. per minute, alternatively 0.15° C. per minute, alternatively about 0.15° C. per minute, alternatively less than 0.15° C. per minute, alternatively 0.1° C. per minute, alternatively about 0.1° C. per minute, alternatively less than 0.1° C. per minute, alternatively 0.05° C. per minute, alternatively about 0.05° C. per minute, alternatively less than 0.05° C. per minute, is contemplated here.

A ramp rate lower limit of 0.05° C. per minute, alternatively about 0.05° C. per minute, alternatively more than 0.05° C. per minute, alternatively 0.1° C. per minute, alternatively about 0.1° C. per minute, alternatively more than 0.1° C. per minute, alternatively 0.15° C. per minute, alternatively about 0.15° C. per minute, alternatively more than 0.15° C. per minute, alternatively 0.2° C. per minute, alternatively about 0.2° C. per minute, alternatively more than 0.2° C. per minute, alternatively 0.25° C. per minute, alternatively about 0.25° C. per minute, alternatively more than 0.25° C. per minute, alternatively 0.3° C. per minute, alternatively about 0.3° C. per minute, alternatively more than 0.3° C. per minute, alternatively 0.35° C. per minute, alternatively about 0.35° C. per minute, alternatively more than 0.35° C. per minute, alternatively 0.4° C. per minute, alternatively about 0.4° C. per minute, is contemplated here.

The first stage of the two stage reaction contemplated here is the esterification step, which is defined here as the reaction of the trialkanolamine with the fatty acid source to form an esteramine intermediate product having a distribution of esters, including at least a diesteramine.

A fatty acid source is defined here as any material that reacts with a trialkanolamine, either directly or after an intermediate step (such as decomposition, hydrolysis, or an exchange of substituents), to provide an esteramine characterized by the following structure:

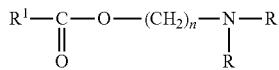

where each n is independently selected from the range of 2 to 6, $(CH_2)_n$ is a straight or branched chain alkyl moiety, $R^1$ is a $C_{5-21}$ straight or branched chain, saturated or unsaturated alkyl group (i.e. a fatty acid source minus the carboxyl carbon atom), and each R is independently selected from an alkanol moiety:

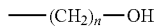

or a fatty carboxylate moiety:

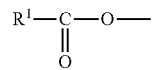

where n, $(CH_2)_n$, and $R^1$ are independently selected from the same choices as above.

One example of a suitable fatty acid source is a straight or branched chain, saturated or unsaturated fatty acid. The alkyl moiety of the fatty acid can be, for example, a $C_{6-22}$ straight or branched chain, saturated or unsaturated alkyl. The upper 22-carbon limit and the lower 6-carbon limit conventionally characterize a fatty alkyl moiety, but are not contemplated to be critical to practice of the present invention. The contemplated fatty acids include but are not limited to oleic, palmitic, erucic, eicosanic and mixtures of these. Other contemplated fatty acid sources are an alkyl ester of a fatty acid, a fat or oil (i.e. a mono-, di-, or triglyceride of one or more fatty acids), a fatty acid anhydride, a fatty acid halide (such as a fatty acid chloride) or mixtures of two or more of these. A person skilled in the art can readily ascertain other suitable fatty acid sources.

A fatty acid feedstock that is a mixture of fatty acids from any naturally occurring fat or oil is also contemplated as a suitable fatty acid source for use in the present reaction. Examples of such fatty acid feedstocks include fatty acids derived from any of the fats or oils listed the table in *Kirk-Othmer Encyclopedia of Chemical Technology*, 4$^{th}$ Ed., Vol. 10, p. 267 (John Wiley & Sons 1993). That table is hereby incorporated by reference. Specific fatty acid source feedstocks contemplated here include fatty acids derived from natural beef tallow and partially hydrogenated beef tallow having an iodine value of from 1 to 90, alternatively having a lower limit of 3, 5, 10, 15, 20, 25, 30, 35, 40, 45, or 50, alternatively having an upper limit of 85, 80, 75, 70, 65, 60, 55, 50, 45, 40, 35, 30, 25, 20, 15, 10, or 5. Hydrogenated, partially hydrogenated, or unhydrogenated soy, palm, palm kernel, rape seed, canola, tall oil, or lard fatty acids, or combinations of them, are also specifically contemplated.

The trialkanolamine has three alkanol moieties independently selected from $C_{1-4}$ alkyl moieties bearing at least one primary or secondary hydroxyl moiety, such as triethanolamine, tripropanolamine, diethanolpropanolamine, propanol diethanolamine, ethanol diisopropanolamine, triisopropanol amine, diethanolisopropanol amine, ethanoldiisobutanolamine, diethanolisobutanolamine, mixtures of these, etc.

The alkanolamine and fatty acid source are combined in any convenient charging ratio of equivalents of fatty alkyl moieties contributed by the fatty acid source, per mol of alkanolamine. For clarity, it should be understood that this ratio is calculated from the number of equivalents of fatty alkyl moieties in the fatty acid source, not necessarily mols of the fatty acid source itself. For example, if the fatty acid source is a fatty acid, the number of mols of fatty acid are directly used for calculating this ratio. On the other hand, if the fatty acid source is a triglyceride, the number of equivalents of fatty acid for calculating this ratio is three times the number of mols of the triglyceride.

For triethanolamine esters, this ratio is sometimes referred to here as a FA/TEA ratio, where "FA" means fatty acid equivalents and "TEA" means mols of triethanolamine.

Specific charging ratio ranges contemplated here have, alternatively, a lower limit of at least 1.2, alternatively at least 1.3, alternatively at least 1.4 alternatively at least 1.5, alternatively at least 1.6, alternatively at least 1.7, alternatively at least 1.8 alternatively at least 1.85, alternatively at least 1.9, alternatively at least 1.95, and an upper limit of at most 2.5, alternatively at most 2.4, alternatively at most 2.3, alternatively at most 2.2, alternatively at most 2.1 alternatively at most 2, alternatively at most 1.95, alternatively at most 1.9, alternatively at most 1.85, alternatively at most 1.8 alternatively at most 1.7, alternatively at most 1.6, alternatively at most 1.5, alternatively at most 1.4, alternatively at most 1.3.

The esterification reaction commonly is promoted by a transesterification or esterification catalyst. The catalyst can be an acid catalyst, a basic catalyst, a salt, a Lewis acid, a Bronsted acid, an enzymatic catalyst, or a combination of two or more of these, or any other suitable catalyst.

Acid catalysts employable in the present process include, but are not limited to, sulfonic acid, sulfuric acid, phosphoric acid, phosphorous acid, p-toluene sulfonic acid, p-TSA, methane sulfonic acid, oxalic acid, hypophosphorous acid, acetic acid, halogen acids (e.g. HF, HI, HBr), $HBF_4$, acid resins (e.g. Amberlite® resins, available from Rohm & Haas Co., Philadelphia, Pa.), Nafion® catalysts available from E. I. du Pont de Nemours and Co., Wilmington Del., or a combination of two or more of these. Alkali metal or alkaline earth metal salts of the last mentioned acids or their organic esters or organic reducing agents, for example thioacetamine, hydrazine, hydroquinone and their derivates, are contemplated.

Hypophosphorous acid is specifically contemplated because it simultaneously functions as a reducing agent. Combinations of this acid or its salts with various other acid catalysts produce end products with better color, and the esterification leads to derivatives with a high fraction of diesters.

Lewis acid catalysts employable in the present process include $Ti(OR)_4$, in which R=Me, i-Pr, or n-Bu; $(Bu)_2SnO$, Sn-oxalate, $(Bu_2ClSn)_2O$; $(tert-Bu_2Sn(OH)Cl)_2$; $Bu_3SnH$; $Yb(OTf)_3$; $La(Ot-Bu)_3$; scandium triflate $(Sc(OTf)_3)$; or a combination of two or more of these.

Exemplary basic catalysts include hydroxides or alkoxides (e.g. NaOMe, NaOH, $Ba(OH)_2$), carbonates (e.g. $K_2CO_3$, $Zr(CO_3)_2$), oxides (e.g. CaO, MgO, SnO, ZnO, $ZrO_2$), or a combination of two or more of these. Exemplary salts include KOAc, $Zr(OAc)_2(OH)_2$, $NaHSO_4$, $KHSO_4$, or a combination of two or more of these.

Another exemplary catalyst is an enzymatic catalyst, such as subtilisin or lipase derived from *Candida Antartica*.

Any other catalyst known to the skilled person to be useful for the selected reaction may also, or instead, be used.

The present inventors have found that if the amount of catalyst used is reduced to less than conventional levels, so the catalyst does not promote fast formation of the esteramine, formation of the amine triester is disfavored more than formation of the amine diester, so the resulting product can have more than 55% diester and less than 25% triester, even if the ramp rate is reduced below the level previously thought to be necessary to provide that result.

Conventional catalysts have been used at a rate of roughly 500-3000 ppm based on the amount of fatty acid source charge. The present invention is carried out by using a suboptimal amount of the catalyst. What is a suboptimal amount will depend on the choice of catalyst and the process conditions, but generally speaking the upper limit of catalyst can be 100 ppm, alternatively 95 ppm, alternatively 90 ppm, alternatively 85 ppm, alternatively 80 ppm, alternatively 75 ppm, alternatively 70 ppm, alternatively 65 ppm, alternatively 60 ppm, alternatively 55 ppm, alternatively 50 ppm, alternatively 45 ppm, alternatively 40 ppm, alternatively 35 ppm, alternatively 30 ppm of catalyst. The contemplated lower limit of catalyst can be any value less than the contemplated upper limit of catalyst addition, such as 5 ppm, alternatively 10 ppm, alternatively 15 ppm, alternatively 20 ppm, alternatively 25 ppm, alternatively 30 ppm, alternatively 35 ppm, alternatively 40 ppm, alternatively 45 ppm, alternatively 50 ppm, alternatively 55 ppm, alternatively 60 ppm, alternatively 65 ppm, alternatively 70 ppm, alternatively 75 ppm of catalyst. Functionally, the amount of catalyst can be expressed as an amount less than optimal to maximize the rate of formation of the diester product. One skilled in the art knows or can readily determine what level of catalyst has been found optimal for formation of the diester product at a high rate, and then reduce the amount of catalyst by at least 25%, alternatively at least 30%, alternatively at least 35%, alternatively at least 40%, alternatively at least 45%, alternatively at least 50%, alternatively at least 55%, alternatively at least 60%, alternatively at least 65%, alternatively at least 70%, alternatively at least 75%, alternatively at least 80%, alternatively at least 85%, alternatively at least 90%, alternatively at least 92%, alternatively at least 94%, alternatively at least 96%, alternatively at least 98%. In certain embodiments, the inventors contemplate that the catalyst can be eliminated, providing the ramp rate is sufficiently low and the cook time is sufficiently long.

The second stage of the two stage reaction, which can be carried out either separately or combined with the first stage reaction, is conversion of the esteramine formed in the first stage reaction to a quaternary ammonium compound, thus forming a quat ester which typically is a mixture of a monoester, di-ester, and tri-ester quaternary ammonium compounds, or "quats."

After the esterification, the crude product is reacted with alkylating agents in order to obtain the quaternary ammonium product. The contemplated alkylating agents include $C_1$-$C_3$ straight or branched chain alkyl halides, phosphates, carbonates, or sulfates, $C_7$-$C_{10}$ aralkyl halides, phosphates or sulfates, and mixtures of these. Examples of preferred alkylating agents include but are not limited to methyl chloride, benzyl chloride, diethyl sulfate, dimethyl carbonate, trimethyl phosphate, dimethyl sulfate or mixtures of these. Choosing the type and amount of alkylating agent employed and suitable alkylating conditions is well within the skill of one in the art. Typically, when dimethyl sulfate is the alkylating agent, 0.7 to 1.0, preferably 0.75 to 0.98 mol dimethyl sulfate per mole of esteramine is satisfactory in yielding the quaternized product.

The proportions of quaternized monoesters, diesters, and triesters in the resulting product can be measured by any suitable analytical technique accepted by those skilled in the art, using standards. One currently useful analytical technique is high-pressure liquid chromatography ("HPLC").

Working Examples 1 and 2

Esteramines are made by combining hydrogenated tallow fatty acid and triethanolamine at the ratio of equivalents of fatty acid to mols of triethanolamine set out in Table 1, using the parts by weight of hypophosphorous acid per million parts by weight of fatty acid set out in Table 1, at a starting temperature of 70° C., then heating the reaction mixture at the ramp rate set out in Table 1 for a time sufficient to reach the maximum reaction temperature set out in Table 1, while drawing vacuum at the level set out in Table 1, until a suitable end point is reached. The resulting product is then quaternized conventionally using dimethylsulfate, yielding an esterquat product having the weight ratio of monoester:diester:triester quats set out in Table 1.

TABLE 1

| Example | Ratio Fatty Acid/TEA | Catalyst (ppm) | Temp ramp (Deg. C. per hr) | T Max (Deg. C.) | Vacuum (mm Hg) | Quat Monoester (wt %) | Quat diester (wt %) | Quat Triester (wt %) |
|---|---|---|---|---|---|---|---|---|
| 1 | 1.94 | 100 | 9.9 | 160 | 168 | 19.7 | 58.9 | 21.4 |
| 2 | 1.95 | 30 | 20 | 165 | 160 | 19.7 | 59.6 | 20.7 |

What is claimed is:

1. A process comprising:
   a. esterifying at least one trialkanolamine and at least one fatty acid source, by heating the trialkanolamine and fatty acid source at an average temperature ramp rate of 0.35° C. per minute or less, wherein the catalyst loading is lower than the optimal amount for formation of the diester product at a high rate, to produce an esteramine; and
   b. reacting the esteramine with an alkylating agent to form an esterquat mixture comprising at least 55 wt. % of a quaternized diester and at most 25 wt. % of a quaternized triester.

2. The process of claim 1, wherein the average ramp rate is from 0.05° C. to 0.35° C. per minute.

3. The process of claim 2, wherein the average ramp rate is from 0.05° C. to 0.3° C. per minute.

4. The process of claim 3, wherein the average ramp rate is from 0.05° C. to 0.2° C. per minute.

5. The process of claim 4, wherein the average ramp rate is from 0.05° C. to 0.1° C. per minute.

6. The process of claim 1, wherein the esterquat mixture comprises at least about 60 wt. % of a diester.

7. The process of claim 1, wherein the esterquat mixture comprises at most about 20 wt. % of a triester.

8. The process of claim 1, wherein the esterifying step is carried out in the presence of a catalyst, wherein the catalyst loading is less than about 100 parts per million parts of fatty acid charged to the reaction vessel.

9. The process of claim 1, wherein the esterifying step is carried out in the presence of a catalyst.

10. The process of claim 9, wherein the catalyst loading is at least 25% lower than the optimal amount for formation of the diester product at a high rate.

11. The process of claim 10, wherein the catalyst loading is at least 50% lower than the optimal amount for formation of the diester product at a high rate.

12. The process of claim 11, wherein the catalyst loading is at least 75% lower than the optimal amount for formation of the diester product at a high rate.

13. The process of claim 12, wherein the catalyst loading is at least 90% lower than the optimal amount for formation of the diester product at a high rate.

14. The process of claim 13, wherein the catalyst loading is at least 98% lower than the optimal amount for formation of the diester product at a high rate.

15. The process of claim 10, wherein the catalyst is phosphorous acid, hypophosphorous acid, sulfonic acid, p-toluene sulfonic acid, methane sulfonic acid, oxalic acid, a Lewis acid, a tin(II) salt, an alkali metal salt of any of the acids, an alkaline earth metal salt of any of the acids, an organic ester of any of the acids, thioacetamine, hydrazine, hydroquinone or their derivatives, or a combination of at least two of them.

16. The process of claim 15, wherein the catalyst comprises hypophosphorous acid.

17. The process of claim 1, wherein the fatty acid source comprises tallow fatty acid.

18. The process of claim 17, wherein the tallow fatty acid has an Iodine value of 3 or less.

19. The process of claim 1, wherein the fatty acid/trialkanolamine weight ratio is at least 1.9.

20. The process of claim 1, wherein the trialkanolamine comprises triethanolamine.

* * * * *